(12) United States Patent
Schmitt et al.

(10) Patent No.: US 12,144,919 B2
(45) Date of Patent: Nov. 19, 2024

(54) FLUID DRAINAGE DEVICE

(71) Applicant: Xpella (Pty) Ltd, Sandton (ZA)

(72) Inventors: Karl-Heinz Schmitt, Sandton (ZA); Clinton Frederick Shahim, Sandton (ZA)

(73) Assignee: XPELLA (PTY) LTD, Sandton (ZA)

( * ) Notice: Subject to any disclaimer, the term of this patent is extended or adjusted under 35 U.S.C. 154(b) by 559 days.

(21) Appl. No.: 17/429,970

(22) PCT Filed: Feb. 11, 2020

(86) PCT No.: PCT/ZA2020/050015
§ 371 (c)(1),
(2) Date: Aug. 11, 2021

(87) PCT Pub. No.: WO2020/168366
PCT Pub. Date: Aug. 20, 2020

(65) Prior Publication Data
US 2022/0143298 A1    May 12, 2022

(30) Foreign Application Priority Data

Feb. 11, 2019 (ZA) .................................. 2019/00880

(51) Int. Cl.
*A61M 1/00*      (2006.01)

(52) U.S. Cl.
CPC .............. *A61M 1/63* (2021.05); *A61M 1/67* (2021.05); *A61M 1/815* (2021.05); *A61M 1/96* (2021.05);
(Continued)

(58) Field of Classification Search
CPC ........ A61M 1/00; A61M 31/00; A61M 37/00; A61M 1/63; A61M 1/67; A61M 1/815;
(Continued)

(56) References Cited

U.S. PATENT DOCUMENTS 1,585,628 A    5/1926   Pfarre
4,578,060 A *   3/1986   Huck ...................... A61M 1/68
                                            604/134
(Continued)

OTHER PUBLICATIONS

International Search Report and Written Opinion for Application No. PCT/ZA2020/050015 dated Apr. 20, 2020 (8 pages).
(Continued)

*Primary Examiner* — Ariana Zimbouski
(74) *Attorney, Agent, or Firm* — Michael Best & Friedrich LLP

(57) ABSTRACT

A fluid drainage device which includes a fluid-receiving volume, a cover which is movable between a first limiting position at which an inlet port is in fluid communication with the volume and a second limiting position at which an outlet port is in fluid communication with the volume, a piston which is movable inside the volume between a first position and a second position, a handle which is moveable in a first direction to cause the piston to move to the first position and to store energy in a spring so that, when the cover is in the first limiting position the piston is moveable by energy released from the spring to reduce pressure in the volume, allowing fluid flow through the inlet port, and wherein movement of the handle in a second direction causes the piston to move to the second position thereby expelling fluid from the volume.

19 Claims, 3 Drawing Sheets

(52) U.S. Cl.
CPC .............. *A61M 1/98* (2021.05); *A61M 1/985* (2021.05); *A61M 1/964* (2021.05)

(58) Field of Classification Search
CPC .......... A61M 1/96; A61M 1/98; A61M 1/985; A61M 1/964; A61M 2205/073
See application file for complete search history.

(56) References Cited

U.S. PATENT DOCUMENTS

| | | | | |
|---|---|---|---|---|
| 4,726,745 | A * | 2/1988 | Adahan | F04B 53/00 417/423.2 |
| 2003/0040687 | A1* | 2/2003 | Boynton | A61M 1/75 601/6 |
| 2013/0041351 | A1* | 2/2013 | Shahim | A61M 1/732 604/543 |
| 2015/0018784 | A1 | 1/2015 | Coulthard et al. | |
| 2016/0106891 | A1 | 4/2016 | Schmitt | |
| 2017/0281399 | A1* | 10/2017 | VanMiddendorp | A61F 5/455 |
| 2018/0353660 | A1* | 12/2018 | Han | A61M 1/815 |

OTHER PUBLICATIONS

International Preliminary Report on Patentability for Application No. PCT/ZA2020/050015 dated Oct. 23, 2020 (5 pages).

* cited by examiner

FLUID DRAINAGE DEVICE

CROSS-REFERENCE TO RELATED APPLICATIONS

The present application is a U.S. National Phase application of PCT/ZA2020/050015 filed Feb. 11, 2020, which claims priority to South African Application No. ZA 2019/00880 filed Feb. 11, 2019, the entire contents of both of which are herein incorporated by reference.

BACKGROUND OF THE INVENTION

This invention relates to the application of a negative pressure to a wound.

In negative pressure wound therapy a negative pressure, i.e. reduced or sub-atmospheric pressure, is applied to a localized area over a wound in order to assist in the closing or healing of the wound. The application of the negative pressure to the wound increases blood flow and also helps to inhibit bacterial growth by drawing fluids, from the wound, which may contain entrained particles which harbour bacteria.

In broad terms the negative pressure wound therapy devices can be placed into one of two categories. In a first category, fluid, typically in the form of exudate and gas, is drawn from a wound which is being treated and is collected in an appropriate container which is discarded once a certain quantity of exudate has been collected.

In a device which falls into the second category, fluid, in the form of exudate, drawn from a wound is not collected in a container but instead is trapped in an appropriate dressing which covers the wound which is being treated. The device is used to maintain a reduced pressure below the wound dressing.

One device which falls into the first category is disclosed in US Patent Application No. 2016/0106891 and includes a piston assembly which controls the flow of fluid into and out of a fluid-receiving volume. An inlet to the volume, and an outlet from the volume, are positioned at appropriate locations on a body of the device. Spring-loaded valves are fixed to the inlet and outlet respectively. The outlet, which functions as a drain from a fluid-receiving chamber, has a relatively weak spring which acts on the respective valve. A difficulty which has been encountered is that, in use, the drain valve does not always seal properly.

On the other hand the force exerted by the spring on the inlet valve can influence the level of reduced pressure which is induced in the volume. Variations in the pressure affect the repeatability of operation of the drainage function.

A device which attempts to address the aforementioned issue has a single opening (inlet/outlet) to a fluid-receiving volume. A valve, of compound construction, which includes an inlet port and a drain port, is operable to connect the inlet port to the opening, and hence to the fluid-receiving volume, so that the device can act in a drainage mode. Alternatively, the valve is operable to connect the drain port to the opening so that fluid from the fluid-receiving volume can be expelled to waste, when required. The device, however, is bulky and cannot readily be employed as a comfortable, user-wearable, device.

An object of the present invention is to provide a fluid drainage device which in a first mode, can function as a device in the first category and, in a second mode, can function as a device in the second category.

SUMMARY OF THE INVENTION

The invention provides a fluid drainage device for use in applying a negative pressure to a wound site, the fluid drainage device including a body with an outer surface, a cylindrical bore, formed in the body, which defines at least a part of a fluid-receiving volume, structure, at least partly on the outer surface of the body, which forms an inlet to and an outlet from the fluid-receiving volume, a cover which includes an inlet port and an outlet port, wherein the cover is movable relative to the body between a first limiting position at which the inlet port is in fluid communication with the inlet and hence with the fluid-receiving volume and fluid flow through the outlet is prevented, and a second limiting position at which the outlet port is in fluid communication with the outlet and hence with the fluid-receiving volume and fluid flow through the inlet is prevented, a piston which is in sealing contact with the bore and which partly bounds the fluid-receiving volume, the piston being movable inside the bore between a first position and a second position, a piston rod which extends from the piston, an energy storage device engaged with the piston rod, a user-actuated handle mechanism which is movable relative to the body in a first direction to cause the piston to move to the first position and to store energy in the energy storage device so that, when the cover is in the first limiting position and the user-actuated handle mechanism is moved relative to the body in a second direction opposite to the first direction, the piston is movable by the action of energy released from the energy storage device away from the first position towards the second position thereby causing a reduction in pressure in the fluid-receiving volume and allowing fluid to flow, in use of the device, to the fluid-receiving volume through the inlet port and, with the piston in the second position, and the cover in the second limiting position, movement of the user-actuable handle mechanism relative to the body in the first direction causes the piston to be moved towards the first position thereby expelling fluid from the fluid-receiving volume through the outlet port.

The energy storage device may be a compression spring.

The handle mechanism may include at least one threaded component which is movable to allow the energy storage device to be loaded with, or to release, energy.

Preferably the handle mechanism includes an inner tubular member which is externally threaded and in which the piston rod and energy storage device are, at least partly, housed, and an outer tubular member which is threadedly engaged with the inner tubular member such that rotation of the outer tubular member in the first direction causes the outer tubular member to move linearly along the inner tubular member, causing energy to be stored in the energy storage device.

The structure may include respective openings positioned at appropriate locations in the outer surface of the body to provide the inlet to, and the outlet from, the fluid-receiving volume. An inlet valve body and an outlet valve body, having fluid flow passages formed there-through, may be in fluid communication with the inlet and outlet respectively. Annular seals may be provided within the passages to provide a leak-proof seal between the inlet and the cover, and the outlet and the cover, respectively. The annular seals may include raised portions on surfaces thereof, to ensure a tight fit with an inner surface of the cover.

The inlet port and outlet port may be positioned on the cover so that when the inlet port is in fluid communication with the inlet, the outlet port is displaced from the outlet and the outlet is closed. Conversely, when the outlet port is in fluid communication with the outlet, the inlet port is displaced from the inlet and the inlet is closed.

The cover may be engaged with the structure through the use of suitable complementary formations e.g. complementary rib and groove formations. This is not limiting.

According to a first embodiment of the invention, the fluid drainage device is suited to drain fluids from a wound. Fluid, in the context of this embodiment of the invention, is primarily in the form of exudate and gas. In use, the fluid drainage device is connected to a first fluid drainage conduit which extends from a wound to the inlet port and through which fluid is to be drained. A second fluid drainage conduit may also be connected to the outlet port through which the fluid is to be expelled. The cover may be moveable relative to the body such that, in the first limiting position, with the inlet port in fluid communication with the inlet to allow fluid to flow through the inlet into the fluid-receiving volume, the outlet is closed.

As the fluid, in the form of exudate and gas, enters the volume, the pressure prevailing in the volume is increased and the piston moves towards the second position. Once the piston has reached a limit, fluid is no longer drawn through the inlet port into the fluid-receiving volume. The cover may be moveable relative to the body such that it is in the second limiting position, with the outlet port in fluid communication with the outlet and with the inlet closed. The handle mechanism may then be actuated so that the piston is moved into the first position, causing the exudate and gas to be expelled from the volume through the outlet to waste. The seal between the inner surface of the cover and the inlet prevents fluid flow through the inlet.

According to a second embodiment of the invention the fluid drainage device is suited for applications where a negative pressure is to be applied to a wound dressing which overlies a wound in a leak-proof manner. Fluid, in the context of this embodiment of the invention, is primarily in the form of gas. Exudate and solids from the wound site are trapped in the wound dressing, which in one respect acts as a filter, and are not drawn into the fluid-receiving volume. In use, the fluid drainage device is connected by a first conduit, which extends from the wound dressing which overlies the wound to the inlet port, through which a negative pressure is to be applied. A second conduit may also be connected to the outlet port through which fluid, in the form of gas, is to be expelled.

The cover may be moveable relative to the body such that in the first limiting position, with the inlet port in fluid communication with the inlet to allow gas to flow through the inlet into the fluid-receiving volume, the outlet is closed. The inlet may be in the form of a Luer connection to provide a leak-proof seal.

As the fluid, in the form of gas, enters the volume, the pressure prevailing in the volume is increased and the piston moves towards the second position. Once the piston has reached a limit, fluid is no longer drawn through the inlet port into the fluid-receiving volume and a negative pressure is no longer applied to the wound dressing. The cover may be moveable relative to the body such that it is in the second limiting position, with the outlet port in fluid communication with the outlet and with the inlet closed. The handle mechanism may then be actuated so that the piston is moved into the first position, causing the gas to be expelled from the volume through the outlet to waste.

In each embodiment, the cover is preferably rotatable relative to the body between the first and second limiting positions.

To prevent inadvertent or unwanted movement of the cover relative to the body the device may include a lock mechanism which automatically retains the cover in the second limiting position when it reaches the second limiting position and which automatically retains the cover in the first limiting position when it reaches the first limiting position. The lock mechanism may be user-actuable in that user actuation is required in order to release the lock mechanism so that the cover can be moved from the second limiting position to the first limiting position, and vice-versa.

BRIEF DESCRIPTION OF THE DRAWINGS

The invention is further described by way of example with reference to the accompanying drawings in which.

DESCRIPTION OF PREFERRED EMBODIMENTS

Figures 1, 2:
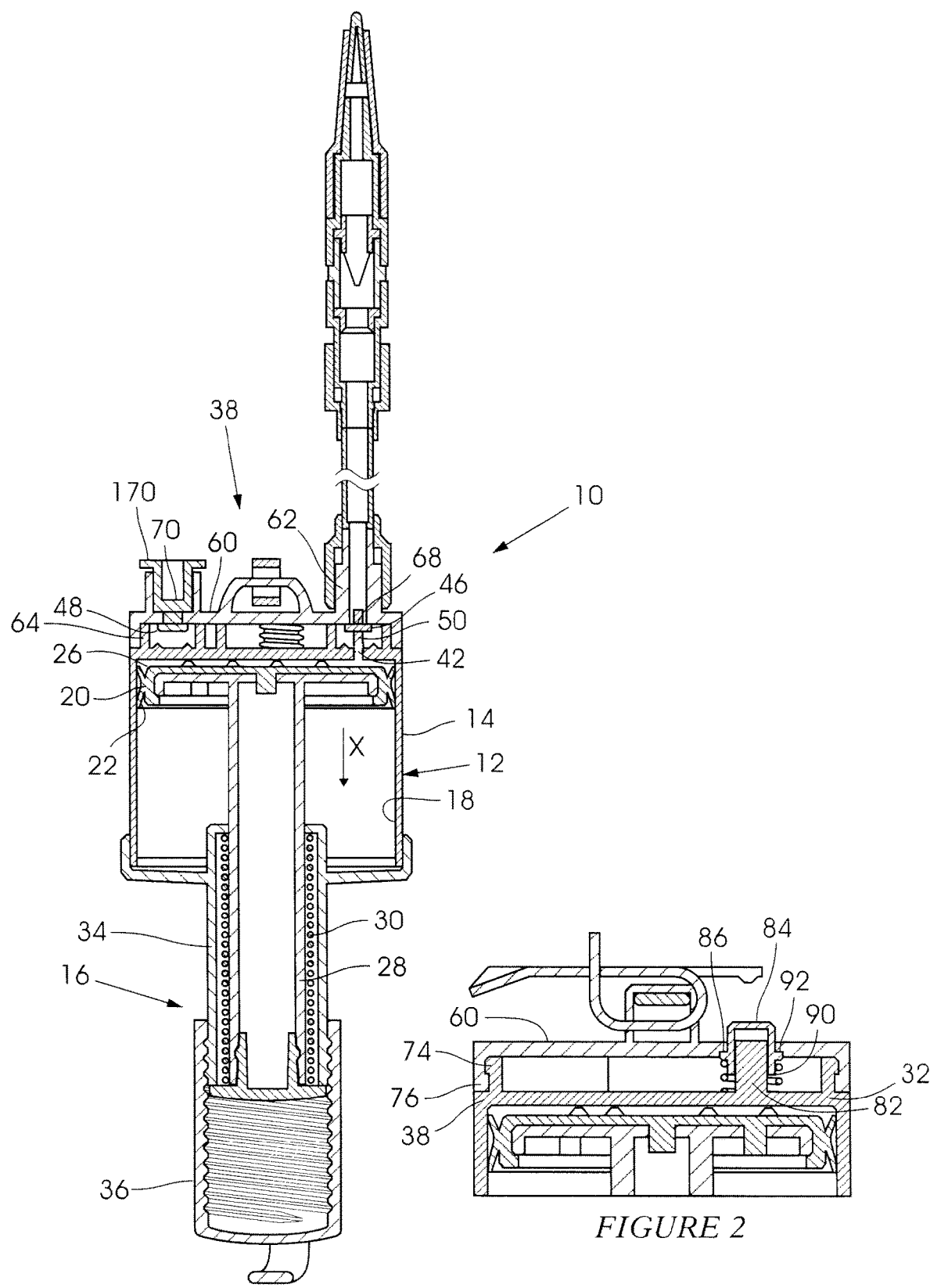
FIG. 1 illustrates, in cross-section, a device according to a first embodiment of the invention, wherein an inlet to the device is open and an outlet from the device is closed.
FIG. 2 is a view on an enlarged scale of a part of the device taken on a line 2-2 in FIG. 1.

FIG. 1 of the accompanying drawings shows, in cross-section, a device 10 for applying a negative pressure to a wound, according to a first embodiment of the invention. The device in FIG. 1 is used to draw fluid, in the form of gas and exudate, from a wound.

The device 10 includes a body 12 with an outer surface 14, and a user-actuable handle mechanism 16 which extends from the body. The body 12 is circular cylindrical in shape and, internally, it has a cylindrical bore 18 with a smooth internal surface.

A piston 20, of complementary shape to the bore 18, is slidingly positioned inside the bore 18. The piston 20 has an external seal 22 which ensures that an intimate seal is established between opposing surfaces of the piston 20 and the bore 18. A fluid-receiving volume 26, of variable size, is defined inside the bore 18 and is partly bounded by the piston 20.

A piston rod 28 extends from the piston 20. A coiled compression spring 30 is engaged with the piston rod 28 and is positioned inside the user-actuable handle mechanism 16.

The handle mechanism 16 includes an inner tubular member 34 which is fixed to the body 12 and which is threadedly engaged with an outer tubular member 36 which is rotatable in relation to the inner tubular member 34. The compression spring 30 is located between opposing surfaces of the piston rod 28 and the inner tubular member 34.

Figures 3, 4:
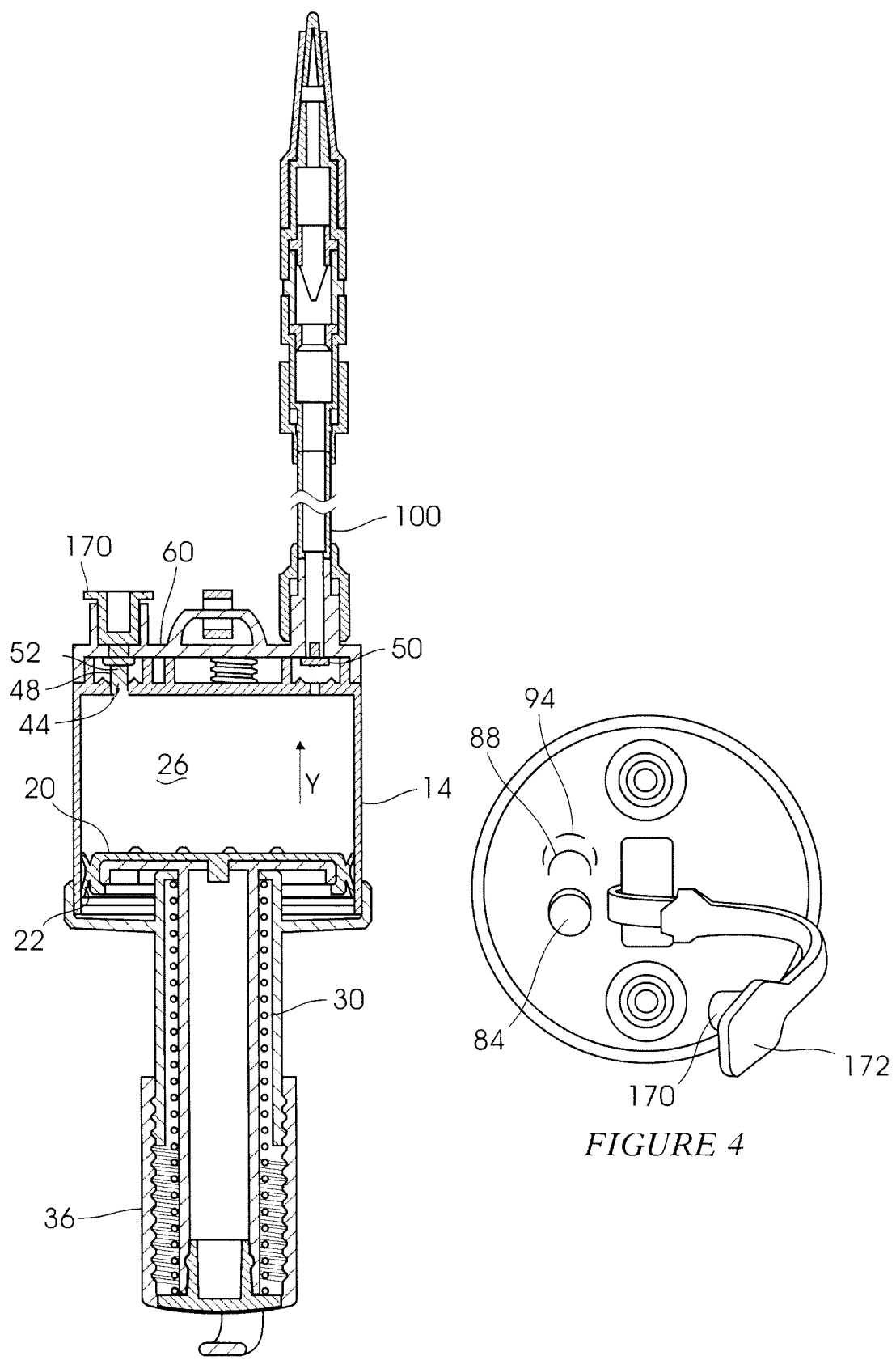
FIG. 3 illustrates in cross-section the device of FIG. 1 with the inlet to the device in a closed position and the outlet from the device in an open position.
FIG. 4 is a plan view of the device.

Structure 38 on the outer surface 14 of the body 12, opposing the piston 20, includes an inlet 42 (see FIG. 1) and an outlet 44 (see FIG. 3). A resilient inlet valve seal 46 is located over the inlet 42 and, a resilient outlet valve seal 48 is positioned over the outlet 44. The inlet valve seal 46 has a passage 50 and the outlet valve seal 48 has a passage 52.

A cover 60 overlies the valve seals 46, 48 and is rotatably engaged with the body 12. The structure 38 includes formations 62 and 64, respectively, which form compartments for the valve seals 46 and 48.

The cover 60 includes an inlet port 68 and an outlet port 70 positioned at appropriate locations on the cover 60. The cover 60 is secured to the structure 38 through the use of complementary formations, shown as complementary ribs and grooves 74 and 76 (FIG. 2). The cover 60 is rotatable to a first limiting position, shown in FIG. 1 and FIG. 2, at which the inlet port 68 is aligned with the passage 50 which in turn is in register with the inlet 42. At this position the outlet valve seal 48 blocks the outlet 44. The cover 60 is movable to a second limiting position, shown in FIG. 3 and FIG. 4, at which the inlet valve seal 46 blocks the inlet 42 and the outlet port 70 is aligned with the outlet passage 52 and the outlet 44.

A compartment is formed for each valve seal. When the cover 60 is rotated relative to the body 12 to the first limiting position (FIG. 1) the inlet port 68 is aligned with the passage 50 and the inlet 42. In the FIG. 3 position, the outlet port 70 is aligned with the passage 52 and the outlet 44.

A locking mechanism 80, carried by the cover 60, is positioned between opposing surfaces of the cover 60 and the structure 38 (FIG. 2). The locking mechanism 80 includes a small shaft 82 which projects from the structure 38. A cap 84 is positioned on the shaft 82. The cap 84 has a small flange 86. The cap 84 can pass into a curved slot 88 (FIG. 4) in the cover 60 but the flange 86 abuts an inner surface of the cover 60. A spring 90 biases the cap 84 towards the cover 60. The cover 60 has two recesses 92 (FIG. 2), 94 (FIG. 4) respectively at opposite ends of the slot 88. When the cover 60 is rotated relative to the body 12 to one limiting position, the flange 86 automatically enters the corresponding recess (94, 96) under the action of the spring 90. The cover 60 is then locked in position and is prevented from being rotated. If the cap 84 is depressed against the action of the spring 90, the flange 86 is disengaged from the recess (94, 96) and the cover 60 can then be rotated until the other limiting position is reached, at which point the flange 86 enters the corresponding recess (96, 94) (when the spring is released). This action prevents further rotation of the cover 60.

FIG. 1 shows the device 10, with a conduit arrangement 100 fixed to the inlet port 68 (which is open). The outlet port 70 is closed. The spring 30 is fully compressed. The fluid-receiving volume 26 is of minimal size but nonetheless has a reduced pressure. The spring 30 constantly urges the piston 20 in a direction away from the structure 38, an action which establishes the reduced pressure inside the volume 26.

As fluid flows into the volume 26, drawn by the reduced pressure in the volume 26, the pressure inside the volume 26 increases slightly and the piston 20 then moves under the action of the spring 30 in a direction X in FIG. 1. This process continues until such time as the volume 26 is filled effectively to a maximum, with fluid.

In order to expel the fluid from the volume 26, the cover 60 is rotated, relative to the body 12 to the FIG. 3 position. The inlet 42 is then closed and the outlet 44 is then open. At this stage, as well, the volume 26 is at a maximum and the spring 30 is in a relaxed state as shown in FIG. 3. The member 36 is rotated to compress the spring 30 and in so doing the piston 20 is moved in a direction Y shown in FIG. 3. Exudate from the volume 26 is expelled through the outlet 44 to waste. The member 36 can then be moved to the FIG. 1 position so that a reduced pressure can again be established in the volume 26.

The body 12 of the device 10 is preferably made from a transparent material so that a visual indication is available to a user of the quantity of the fluid in the volume 26.

The arrangement of the cover 60 relative to the structure 38 is such that the inlet 42 is only engageable with the inlet port 68 when the cover 60 is in a first limiting position, shown in FIG. 1, and the outlet 44 is only engageable with the outlet port 70 when the cover 60 is in a second limiting position, shown in FIG. 3. When the cover 60 is in the first limiting position (see FIG. 1), the inlet 42 overlies, and is in fluid communication with, the inlet port 68 to allow fluid flow into the volume 26. In this position, the outlet 44 is displaced from the outlet port 70 and the seal 50 bears against the inner surface 52 of the cover 60, providing a leak-proof seal at the outlet 44.

FIG. 2 shows the cover 60 in the second limiting position. In this position, the outlet port 70 overlies and is in fluid communication with outlet 44, allowing fluid to be expelled from the volume 26. The inlet port 68 is displaced from the inlet 42 and the seal 48 bears against an inner surface of the cover 60, providing a leak proof seal at the inlet 42.

In use, a first elongate flexible drainage conduit 100 is connected to the inlet port 68. According to a first embodiment of the invention, a free end of the conduit 100 is positioned, as is known in the art, in a body cavity from which fluid is to be drained (not shown). A second elongate flexible drainage conduit (not shown) is connected to the outlet port 70. A free end of the conduit is connectable to a suitable waste container. At this stage (shown in FIG. 2) the outer tubular member 36 is fully engaged with the inner tubular member 28 and the spring 30 is loaded with energy. The piston 20 is in the first position and the volume 26 has a minimum value.

The cover 60 is manually rotated such that it is in the first limiting position, shown in FIG. 1. In this position, the inlet port 68 is in the fluid communication with the inlet 42 and the inlet is open and the outlet 44 is closed. The outer tubular member 36 is rotated in a first direction relative to the inner member 34, causing the outer tubular member 36 to ride over the threads and move in an axial direction away from the body 12. The handle 16 is then in an extended configuration as shown in FIG. 1 and, as a consequence, the spring 30 releases energy thereby pulling the piston 20 away from the top surface 14 towards a base of the container body 12.

As the volume 26 increases, the pressure within the volume 26 decreases and fluid is drawn from the wound through the inlet 42 and into the fluid-receiving volume 26. Once a quantity of fluid has been drained, the piston 20 would have reached a limiting position and the pressure in the volume 26 would have increased to atmospheric pressure. The drainage of fluid into the volume 26 then stops Fluid in the volume 26, in the form of exudate and gas, can be drained by rotating the cover 60 such that it is in the second limiting position, shown in FIG. 3, with the outlet port 70 in fluid communication with the outlet 44. The outlet 44 is open and the inlet 42 is closed. The outer member 36 is then rotated in a direction to cause loading of the spring 30, and so that the piston 20 pushes exudate and gas to waste through the outlet 44.

Figure 5:
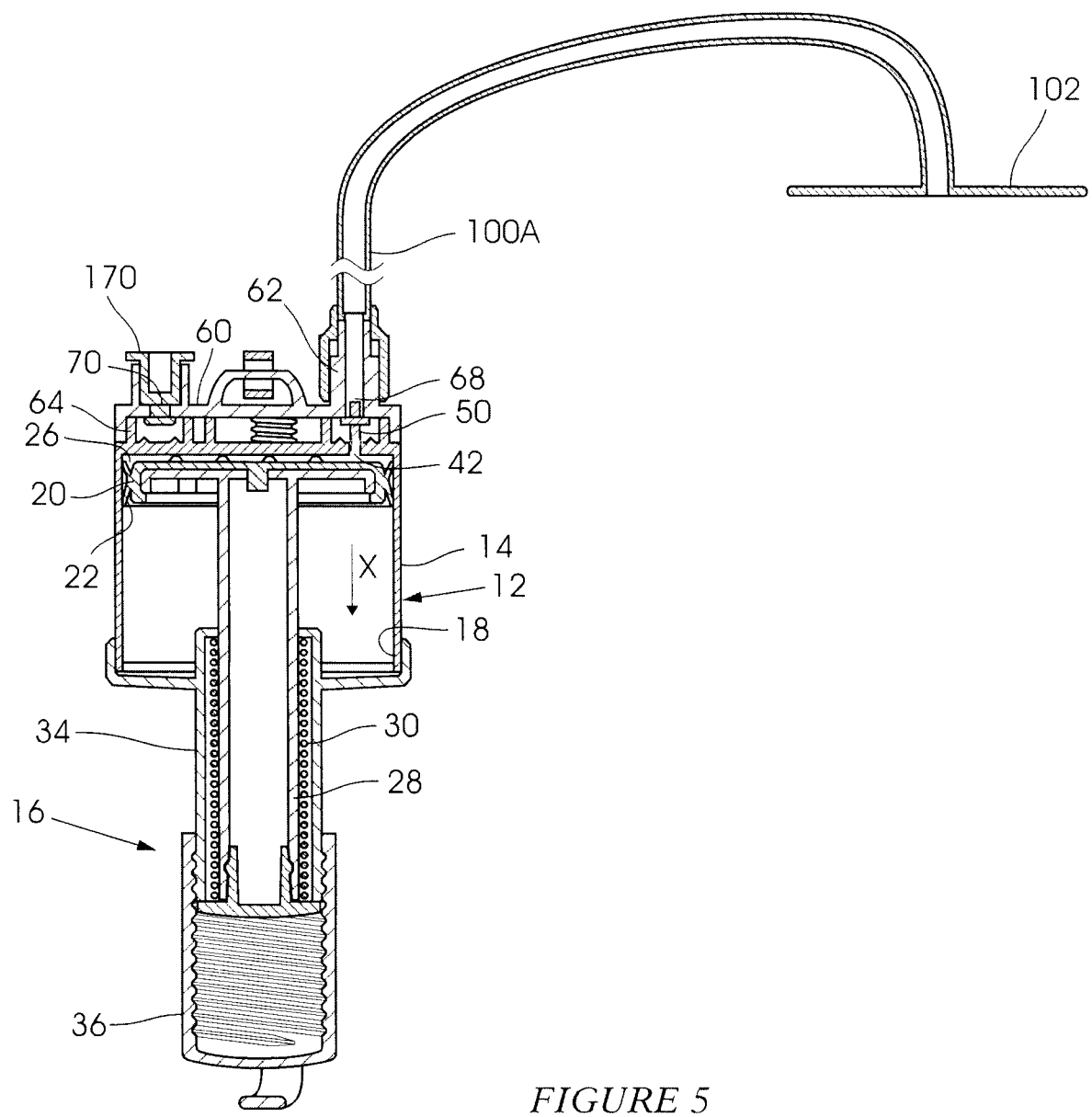
FIG. 5 illustrates, in cross-section, a device according to a second embodiment of the invention, wherein an inlet to the device is open and an outlet from the device is closed.

FIG. 5 shows a second embodiment 10A of the invention which has substantial similarities to the device 10. Hence the device 10A is not described in details. The differences between the devices 10 and 10A are apparent from an inspection of FIG. 1 and FIG. 5. The device 10A is used to apply a negative pressure to a wound dressing which overlies a wound and fluid, in the form of gas, is drained from the wound. Exudate and solids from the wound are trapped in the wound dressing.

Referring to FIG. 5, the first elongate conduit 100A is connected to the inlet port 68, which is in the form of a Luer connection to provide a leak-proof seal. A free end of the conduit 100A is connected, as is known in the art, to a wound dressing 102, shown notionally in FIG. 5, which overlies and is in leak-proof communication with a wound to be treated (not shown). At this stage (shown in FIG. 2) the outer tubular member 36 is fully engaged with the inner tubular member 28 and the spring 30 is loaded with energy. The piston 20 is in the first position and the volume 26 has a minimum value, with a reduced pressure.

The cover 60 is manually rotated such that it is in the first limiting position, shown in FIG. 1. In this position, the inlet port 68 is in the fluid communication with the inlet 42 and the inlet is open and the outlet 44 is closed. The outer tubular member 36 is rotated in a first direction relative to the inner member 34, causing the outer tubular member 36 to ride over the threads and move in an axial direction away from the body 12. The handle 16 is then in an extended configuration as shown in FIG. 1 and, as a consequence, the spring 30 releases energy thereby pulling the piston 20 away from the top surface 14 towards a base of the container body 12.

As the volume 26 increases, the pressure within the volume 26 decreases and a negative pressure is applied to the wound dressing 102. Once the piston 20 has reached a limiting position, the pressure in the volume 26 would have increased to atmospheric pressure. The application of a negative pressure to the wound dressing 102 then stops.

Fluid, primarily in the form of gas in the volume 26, can be expelled by rotating the cover 60 such that it is in the second limiting position, shown in FIG. 3, with the outlet port 70 in fluid communication with the outlet 44. The outlet 44 is open and the inlet 42 is closed. The outer member 36 is then rotated in a direction to cause loading of the spring 30, and so that the piston 20 pushes gas to waste through the outlet 44.

The various figures contain different views of a plug 170 which is attached to a flexible tie 172. The tie is secured to the cover 60. FIG. 1 shows the plug 170 engaged with the outlet port 70. The plug then seals the outlet port 70 and prevents fluid from dripping from the cover after the volume 26 has been emptied.

The invention claimed is:

1. A fluid drainage device (10, 10A) for use in applying a negative pressure to a wound site, the fluid drainage device (10, 10A) including a body (12) with an outer surface (14), a cylindrical bore (18), formed in the body (12), which defines at least part of a fluid-receiving volume (26), structure (38), at least partly on the outer surface (14) of the body (12), which forms an inlet (42) to and an outlet (44) from the fluid-receiving volume (26), a cover (60) which includes an inlet port (68) and an outlet port (70), wherein the cover (60) is movable relative to the body (12) between a first limiting position at which the inlet port (68) is in fluid communication with the inlet (42) and hence with the fluid-receiving volume (26) and fluid flow through the outlet (44) is prevented, and a second limiting position at which the outlet port (70) is in fluid communication with the outlet (44) and hence the fluid-receiving volume (26) and fluid flow through the inlet (42) is prevented, a piston (20) which is in sealing contact with the bore (18) and which partly bounds the fluid-receiving volume (26), the piston (20) being movable inside the bore (18) between a first position and a second position, a piston rod (28) which extends from the piston (20), an energy storage device (30) engaged with the piston rod (28), a user-actuated handle mechanism (16) which is moveable relative to the body (12) in a first direction to cause the piston (20) to move to the first position and to store energy in the energy storage device (30) so that, when the cover (60) is in the first limiting position and the user-actuated handle mechanism (16) is moved relative to the body (12) in a second direction opposite the first direction, the piston (20) is moveable by the action of energy released from the energy storage device (30) away from the first position towards the second position thereby causing a reduction in pressure in the fluid-receiving volume (26) and allowing fluid flow, in use of the device (10, 10A), to the fluid-receiving volume (26) through the inlet port (68) and, with the piston (20) in the second position and with the cover (60) in the second limiting position, movement of the user-actuable handle mechanism (16) relative to the body (12) in the first direction causes the piston (20) to be moved towards the first position thereby expelling fluid from the fluid-receiving volume (26) through the outlet port (70), wherein the structure (38) includes respective openings in the outer surface (14) of the body (12) to provide the inlet (42) and the outlet (44) from, the fluid receiving volume (26).

2. The fluid drainage device (10, 10A) according to claim 1 wherein the energy storage device (30) is a compression spring.

3. The fluid drainage device (10, 10A) according to claim 1 wherein the handle mechanism (16) includes at least one threaded component which is movable to allow the energy storage device (30) to be loaded with, or to release, energy.

4. The fluid drainage device (10, 10A) according to claim 3 wherein the handle mechanism (16) includes an inner tubular member (34) which is externally threaded and in which the piston rod (28) and energy storage device (30) are, at least partly, housed, and an outer tubular member (36) which is threadedly engaged with the inner tubular member (34) such that rotation of the outer tubular member (36) in the first direction causes the outer tubular member (36) to move linearly along the inner tubular member (34), causing energy to be stored in the energy storage device (30).

5. The fluid drainage device (10, 10A) according to claim 1 wherein an inlet valve body and an outlet valve body, having respective flow passage formed there-through, are in fluid communication with the inlet (42) and the outlet (44) respectively.

6. The fluid drainage device (10, 10A) according to claim 5 wherein annular seals (46, 48) are provided within the passages to provide a leak-proof seal between the inlet (42) and the cover (60), and the outlet (44) and the cover (60), respectively.

7. The fluid drainage device (10, 10A) according to claim 6 wherein the annular seals (46, 48) include raised portions on surfaces thereof to ensure a tight fit with an inner surface of the cover (60).

8. The fluid drainage device (10, 10A) according to claim 7 wherein the inlet port (68) and the outlet port (70) are positioned on the cover (60) so that when the inlet port (68) is in fluid communication with the inlet (42), the outlet port (70) is displaced from the outlet (44) and the outlet (44) is closed, and when the outlet port (70) is in fluid communication with the outlet (44), the inlet port (68) is displaced from the inlet (42) and the inlet (42) is closed.

9. The fluid drainage device (10, 10A) according to claim 8 wherein the cover (60) is engaged with the structure (38) through the use of complementary formations (74, 76).

10. The fluid drainage device (10, 10A) according to claim 1 wherein the inlet port (68) and the outlet port (70) are positioned on the cover (60) so that when the inlet port (68) is in fluid communication with the inlet (42), the outlet port (70) is displaced from the outlet (44) and the outlet (44) is closed, and when the outlet port (70) is in fluid communication with the outlet (44), the inlet port (68) is displaced from the inlet (42) and the inlet (42) is closed.

11. The fluid drainage device (10, 10A) according to claim 1 wherein the cover (60) is engaged with the structure (38) through the use of complementary formations (74, 76).

12. The fluid drainage device (10, 10A) according to claim 11 wherein the complementary formations (74, 76) are rib and groove formations.

13. The fluid drainage device (10, 10A) according to claim 11 wherein the complementary formations (74, 76) are rib and groove formations.

14. The fluid drainage device (10, 10A) according to claim 13 wherein the cover (60) is rotatable relative to the body (12) between the first and second limiting positions.

15. The fluid drainage device (10, 10A) according to claim 14 wherein the device (10) includes a lock mechanism (80) which automatically retains the cover (60) in the second limiting position when it reaches the second limiting position and which automatically retains the cover (60) in the first limiting position when it reaches the first limiting position.

16. The fluid drainage device (10, 10A) according to claim 1 wherein the cover (60) is rotatable relative to the body (12) between the first and second limiting positions.

17. The fluid drainage device (10, 10A) according to claim 1 wherein the device (10) includes a lock mechanism (80) which automatically retains the cover (60) in the second limiting position when it reaches the second limiting position and which automatically retains the cover (60) in the first limiting position when it reaches the first limiting position.

18. The fluid drainage device (10, 10A) according to claim 17 wherein the lock mechanism (80) is user-actuable in that user actuation is required in order to release the lock mechanism (80) so that the cover (60) can be moved from the second limiting position to the first limiting position, and vice-versa.

19. The fluid drainage device (10A) according to claim 1 in combination with a wound dressing (102) which is connected to the inlet port (68) by means of a conduit (100A).

* * * * *